United States Patent [19]

Sen

[11] Patent Number: 4,804,744

[45] Date of Patent: Feb. 14, 1989

[54] OSTEOGENIC FACTORS

[75] Inventor: Arup Sen, Los Angeles, Calif.

[73] Assignee: International Genetic Engineering, Inc., Santa Monica, Calif.

[21] Appl. No.: 904,563

[22] Filed: Sep. 5, 1986

Related U.S. Application Data

[63] Continuation of Ser. No. 568,167, Jan. 4, 1984, abandoned.

[51] Int. Cl.$^4$ .................. A61K 35/32; C07K 13/00
[52] U.S. Cl. .................................. 530/350; 530/840; 424/95
[58] Field of Search .................. 530/350, 840; 424/95

[56] References Cited

U.S. PATENT DOCUMENTS

| | | | |
|---|---|---|---|
| 4,294,753 | 10/1981 | Urist | 424/95 |
| 4,434,094 | 2/1984 | Seyedin et al. | 424/95 |
| 4,563,350 | 1/1986 | Nathan et al. | 424/95 |
| 4,627,982 | 12/1986 | Seyedin et al. | 424/95 |

FOREIGN PATENT DOCUMENTS 0169016 1/1986 European Pat. Off. .

OTHER PUBLICATIONS

Urist et al., "A Soluble Bone Morphogenetic Protein Extracted from Bone Matrix with a Mixed Aqueous and Nonaqueous Solvent", *Proc. Soc. Exp. Bio. and Med.*, 162, 48–53, (1979).

Termine et al., "Mineral and Collagen-Binding Proteins of Fetal Calf Bone", *Journal of Biological Chemistry*, No. 20, Issue of Oct. 25, pp. 10403–10408, 1981.

Takaoka et al., Purification of a Bone-Inducing Substance (Osteogenic Factor), from a Murine Osteosarcoma, Biomed. Res., 2(5), 466–471, (1981).

Takaoka et al., Clin. Orthop. & Rel. Res., 148, 274, (1980).

Takaoka et al., Clin. Orthop. & Rel. Res., 164, 265–270, (1982).

Mizutani and Urist, Clin. Ortho. Rel. Res., 171, 215–223, (1982).

Seyedin et al., Proc. Natl. Acad. Sci., 82, 2267–2271, (Apr. 1985).

*Primary Examiner*—Maurice J. Welsh
*Assistant Examiner*—Nathan M. Nutter
*Attorney, Agent, or Firm*—Marshall, O'Toole, Gerstein, Murray & Bicknell

[57] ABSTRACT

A protein extracted from demineralized bone matrix exhibiting bone-inducing activity is disclosed as well as a method for the rapid isolation and purification of the protein to an essentially homogeneous state. Pharmaceutically acceptable compositions containing the bone-inducing protein and suitable pharmaceutical carriers are also described.

8 Claims, 2 Drawing Sheets

OSTEOGENIC FACTORS

This is a continuation of application Ser. No. 568,167, filed Jan. 4, 1984 and now abandoned.

BACKGROUND

Bone is a highly specialized connective tissue with unique mechanical properties derived from its extensive matrix structure. A network of fibrous bundles composed of the protein collagen is presumed to provide the tension-resistant behavior of bone. In addition other materials including proteoglycans, noncollageous protein, lipids and acidic proteins associated with a mineral phase consisting primarily of poorly crystallized hydroxyapatite are deposited in the extensive matrix architecture of bone. Bone tissue is continuously renewed throughout the life of mammals. This physiologic process might serve to maintain the properties of a young tissue.

The processes of bone formation and renewal are carried out by specialized cells. Osteogenesis vis-a-vis morphogenesis and growth of bone is presumably carried out by the "osteoblasts" (bone-forming cells). Remodeling of bone is apparently brought about by an interplay between the activities of the bone-resorbing cells called "osteoclasts" and the bone-forming osteoblasts. The bony skeleton is thus not only an architectural structure with a mechanical function but also is a living tissue capable of growth, modeling, remodeling and repair. Since these processes are carried out by specialized living cells, chemical (pharmaceutical/hormonal), physical and physicochemical alterations can affect the quality, quantity and shaping of bone tissue.

A variety of pathological disorders as well as physical stress (for example, fracture) necessitate active formation of bone tissue at rates that are significantly higher than that which can be supported by the normal milieu of the body. It is thus of value to identify physiologically acceptable chemical agents (hormones/pharmaceuticals/growth factors) that can induce the formation of bone at a predetermined site. Such agents could either provide a permissive matrix structure for the deposition of bone-forming cells or cause growth stimulation of bone-forming cells or induce the differentiation of appropriate progenitors of bone-forming cells.

The presence of proteinaceous and prostaglandin-like growth stimulators for osteoblasts has been examined, see Raisz, L. G., et al., The New England Journal of Medicine, Vol. 309, No. 1, pp. 29–35 (1983) and Raisz, L. G., et al., The New England Journal of Medicine, Vol. 309, No. 2, pp. 83–89 (1983).

Urist et al. have been able to provide evidence that bone matris-associated noncollagenous proteins can be isolated by dissociative treatment of demineralized bone powder and that this mixture of extracted materials as well as partially fractionated materials obtained therefrom contain bone morphogenetic activity, see Urist, M. R., et al., Proc. Natl. Acad. Sci. USA, Vol. 76, No. 4, pp. 1828–1832 (1979); Urist, M. R., et al., Proceedings of The Society of Experimental Biology and Medicine, Vol. 162, pp. 48–53 (1979); Hanamura, H., et al., Clinical Orthopedics, Vol. 148, pp. 281–290 (1980); Urist, M. R., U. S. Pat. No. 4,294,753 (1981); Urist, M. R., et al., Clinical Orthopedics, Vol. 162, pp. 219–232 (1982); and Urist, M. R., et al., Science, Vol. 220, pp. 680–686 (1983).

Baylink and his collaborators have been able to identify a separate type of activity which presumably couples bone resorption with new bone formation, see Howard, G. A., et al., Metabolic Bone Disease and Related Research, Vol. 2, pp. 131–135 (1980); Farley, J. R., et al., Biochemistry, Vol. 21, pp. 3502–3507 (1982) and Farley, J. R., et al., Vol. 21, pp. 3508–3513 (1982). The activity which Farley et al. obtained from bone matrix involves a different extraction procedure than that of the present invention or that of Urist, supra, it has a larger molecular weight and was called "skeletal growth factor" or "skeletal coupling factor".

The procedure and techniques known in the art for obtaining putative osteogenic activities suffer from several flaws. The isolation procedures are prolonged, ill-defined and incomplete. As such, a definitive association of the activity with a chemically characterized, highly purified protein preparation has not been established. A protein of approximately 17,000 daltons obtained from calf bone powder has been termed "bone morphogenetic protein", see Urist, M. R., et al., Science, Vol. 220, pp. 680–686 (1983); it is claimed to induce efficient bone formation especially when present in a multimolecular assembly with certain other bone-derived proteins which in the absence of the 17,000 dalton protein are non-osteogenic. Urist et al., Proceedings of The Society of Experimental Biology and Medicine, Vol. 173, pp. 194–199 (1983), also identified a 17,000 to 18,000 dalton protein from human bone; this protein is claimed to induce efficient bone formation when administered together with 24,000 and 14,000 dalton human bone-derived proteins. The 24,000 and 14,000 dalton proteins are osteogenically inactive when used without the 17,000 to 18,000 dalton protein but might serve as carriers of the active 17,000 to 18,000 dalton human bone protein. Less pure preparations containing proteins of molecular weights between 17,000 and 23,000 daltons and claimed to possess bone-morphogenetic activities have been isolated from sources such as mouse osteosarcoma, see Hanamura, H., et al., Clinical Orthopedics, Vol. 153, pp. 232–240 (1980), rabbit dentin, see Conover, M. A., and Urist, M. R., The Chemistry and Biology of Mineralized Connective Tissues, Elsevier North Holland, Inc., pp. 597–606 (1981). Protein preparations used in most of the osteogenic activity measurement experimentations described in the literature to date have been of insufficient purity and thus have not led to the identification of the specific molecular entities responsible for the observed activities. Furthermore, studies reported to date have failed to reveal any chemical (biochemical) relationship between the active protein species present in the various "bone morphogenetic protein" preparations.

This invention involves the isolation, purification to an essentially homogeneous state, and the chemical description of a bone matrix protein, characterized by a novel chemical composition and amino acid sequence. This protein induces bone formation at a predetermined site when it is applied either alone or in admixture with a suitable pharmaceutically acceptable carrier. Based on the ability of this essentially homogeneous protein to induce bone development, it is sometimes referred to herein as the "primary osteogenic factor" of bone. Two additional bone-derived protein preparations unrelated to the previously described protein are also described; these proteins by themselves do not induce bone formation but may positively influence osteogenesis when used inconjunction with the primary osteogenic factor.

The invention also concerns the isolation and characterization of immunologically related osteogenic proteins from various bone sources. A rapid, precise and efficient isolation technique is described for the purification of the members of an immunologically related family of equivalent proteins related to each of the above-noted protein species obtained from bone.

SUMMARY OF THE INVENTION

The present invention is directed to proteins which exhibit the ability to promote or stimulate osteogenesis at desired locations in mammals. Using procedures well known in the art, for example, chemical, enzymatic or recombinant DNA techniques, it may be possible to obtain polypeptides derived from the osteogenic proteins described herein which exhibit the ability to promote or stimulate osteogenesis. Proteins or polypeptides that are or can be converted to osteogenically active species which are immunologically related to the primary osteogenic factor (the primary osteogenic factor is frequently referred to as P3 herein) or fragments thereof are also considered to be within the scope of the present invention. Active entities, referred to herein as "active polypeptides", include any portion of the proteins or polypeptides which are the subject of the present invention and their functional derivatives which can be produced by conventional procedures such as chemical synthesis or recombinant DNA techniques. Derivatives of such active polypeptides can include, for example, chemically or enzymatically modified polypeptides; fusion proteins; or polypeptides bound to a suitable carrier substance such as a polymer, etc. The present invention is also directed to a method for isolating, purifying and characterizing the proteins and to a method of using one or more of the proteins and/or active polypeptides and/or immunologically related entities as pharmaceutical agents for the stimulation of bone growth in mammals. Pharmaceutically acceptable compositions comprised of one or more of the proteins and/or active polypeptides and/or immunologically related entities in combination with a pharmaceutically acceptable carrier are also disclosed herein. Such compositions can optionally contain other bioactive materials or other ingredients which aid in the administration of the composition or add to the effectiveness of the composition.

As used herein, the term "immunologically related" is meant to include any polypeptide which shows binding and/or recognition to antigen-binding sites in antibodies raised or manufactured against the protein. The term "osteogenesis" means formation of new bone or induction of growth of pre-existing bones at specific sites in response to local administration (for example, implantation) of an active preparation in a pharmaceutically acceptable manner. The term "osteogenic amount" refers to an amount of the osteogenic protein and/or active polypeptide and/or immunologically related entity sufficient to provide the desired effect. The term "osteogenically active" or "osteogenic" means that the preparation has the capability to promote or induce osteogenesis.

DETAILED DESCRIPTION OF THE INVENTION

Figure 1:
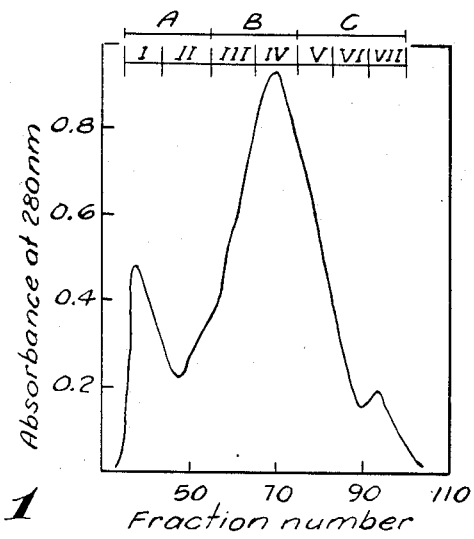
FIG. 1 represents the elution profile obtained by Sepharose CL-6B column chromatography of the proteins obtained in an eight hour extraction of demineralized calf bone powder with 4M GuHCl-0.01M Tris.HCl buffer (pH 7.0).

Using chromatographic procedures known in the art, each of several proteins have been purified to an essentially homogeneous state starting from crude protein extracts of demineralized bone powder. As judged by the migration of these proteins in polyacrylamide gels under dissociating, reducing conditions, using the procedure essentially as described by Laemmli, U. K., Nature, Vol. 227, pp. 680-685 (1970), different protein species have been assigned numbers such as P1, P2 and the like in the order of decreasing apparent molecular weight. Equivalent proteins have been obtained from bones of different mammals. For example, equivalent proteins corresponding to the primary osteogenic factor with an assigned name of P3 herein, have been isolated from bones of several mammals. These represent a family of immunologically related P3 proteins, a member of which purified to an essentially homogeneous state from calf bone according to the procedures essentially as described herein, has an apparent molecular weight of 22,000 to 24,000 daltons, and an amino terminus sequence and an amino acid composition as described later herein. Similarly, a P3 protein isolated from human bone and purified to an essentially homogeneous state according to the procedure essentially as described herein is immunologically related to the calf P3 protein, has an apparent molecular weight of 22,000 to 24,000 daltons and an amino acid composition as described later herein.

In addition, two unrelated protein preparations designated herein as P2 and P4 have also been isolated from bone of several different mammalian species. A family of P2 proteins, each member isolated from a particular mammalian bone source, has been characterized. A typical P2 protein isolated from calf bone has an apparent molecular weight of 30,000 to 33,000 daltons, is incapable of inducing osteogenesis in the absence of a representative P3 protein, and has an amino terminus sequence as described later herein. Immunologically related P2 protein has also been isolated according to the procedure essentially as described herein from human bone.

In a similar manner, a family of P4 proteins has been isolated according to the procedures described herein. In the stage of purification accomplished from calf bone, the P4 preparation consists of two major components which are incapable of inducing osteogenesis in the absence of P3 protein, both having an apparent molecular weight of about 16,000 to 18,000 daltons and are characterized by amino terminus amino acid sequences as described later herein. Immunologically related members of this P4 protein family which are also incapable of inducing osteogenesis in the absence of P3 protein having been isolated from human bone according to the procedure described herein.

As used herein, the term "essentially homogeneous" is meant to describe a protein which is homogeneous by one or more purity or homogeneity characteristics normally used by those of skill in the art of protein chemistry. For example, an essentially homogeneous protein will show constant and reproducible characteristics within standard experimental deviations for parameters such as the following: amino acid analysis, amino- or carboxyl-terminus sequence, band pattern on conventional polyacrylamide gel electrophoresis (PAGE) or other chromatographic techniques, molecular weight, isoelectric point, immunological properties and other such parameters. The terms, however, are not meant to exclude artificial or synthetic mixtures of the protein with other proteins. Thus, the present invention includes mixtures of two or more essentially homogeneous proteins, for example, mixtures of P3 and P4; of P3 and P2; of P2, P3 and P4; of P3 with neutral matrix protein(s); of P3 with other yet to be discovered osteogenic proteins; of P3's from two or more mammalian sources, and the like. The terms are also not meant to exclude the presence of minor impurities which do not interfere with the biological activity of the protein, and which may be present, for example, due to incomplete purification.

The application of the osteogenic factors can be conveniently accomplished by administering, such as by implanting, a lyophilized preparation or suspension of one or more of the osteogenic proteins and/or one or more active polypeptide and/or one or more immunologically related entities in sufficient quantity to promote osteogenesis at the desired site. Alternatively, pharmaceutically acceptable compositions can be used which are comprised of one or more of the osteogenic proteins and/or one or more of the active polypeptides and/or one or more of the immunologically related entities described herein and a pharmaceutically acceptable matrix such as collagenous proteins or matrix material derived from powdered bone extracted with strong denaturing agents, or other pharmaceutically acceptable carriers.

The following example is included to further illustrate the invention but is not to be construed as a limitation thereon.

EXAMPLE

Isolation Of The Osteogenic Factors

Bone Processing: In a typical preparation, long bones (ends of long bones) from a mammal (for example, ankles from calves, femur heads or vertebral column from human bones, the total tibia and fibula from rats) are processed and demineralized using well known conventional procedures such as those described in Urist, M. R., U.S. Pat. No. 4,294,753 (1981). These and all other references cited herein are incorporated herein by reference.

A convenient method of processing and demineralizing bone is as follows:

The periosteal layer surrounding the bone (preferably the bone is obtained from a young mammal and kept refrigerated until processing) is removed by mechanical means and then the marrow from the central cavity of the bone is removed by washing with cold water. The bone is pulverized into small particles [generally 1 to 2 millimeters (mm) in diameter] by conventional means, for example, using a Wiley mill. The particles are then washed exensively with a buffered saline solution such as a 0.15M NaCl-0.1M Tris.HCl buffer (pH 7.0) to remove most of the lipids and remaining blood. The particles are further reduced in size by shearing, for example, using a polytron homogenizer (Brinkman Instruments) so that particles of approximately 500 microns ($\mu$) in diameter or less are obtained. The homogenized particles are washed with buffered saline such as that noted above and water, then with ethanol and finally with ether. The washed homogenized particles are then vacuum or air dried; this "bone powder" can be stored at $-80°$ C. for prolonged periods of time.

For efficient demineralization and protein extraction the bone powder is sieved to obtain particles having a size range of about 75 to 500$\mu$ in diameter. Demineralization (that is, the removal of calcium phosphate from the bone matrix) is achieved by repeated washes with a hydrochloric acid (HCl) solution, for example, by stirring bone powder for one hour with about 10 to 15 milliliters (ml) of 0.5 normal (N) HCl per gram (g) dry weight of bone powder, decanting the liquid and then repeating this process three or four times. The demineralized bone powder is then washed extensively with deionized distilled water until the pH approaches neutrality. The water is removed from the demineralized bone powder by washing with ethanol, then ether, and then drying. The demineralized bone powder can be stored at ultralow temperatures (for example, $-20°$ to $-80°$ C.). Demineralization of the bone powder can also be accomplished using other well known procedures, for example, using a chelator such as ethylenediaminetetraacetic acid.

To determine if the treated bone powder is sufficiently demineralized after HCl treatment to be ready for the extraction of of the bone-matrix proteins, the water-rinsed powder is tested for mineral content [(that is, calcium content), for example, by the method of von Kossa, see J. von Kossa, Ziegler's Beitr. 29, 163 (1901)]. When the von Kossa stain is negative the treated bone powder is sufficiently demineralized to be ready for the extraction of proteins.

Extraction and Separation of Proteins From Demineralized Bone Powder

Demineralized bone powder, prepared as described above, is extracted by constant stirring with an aqueous solution of about 2 to 8 molar (M) guanidinium-hydrochloride (GuHCl) in a buffer such as Trizma-hydrochloride (Tris.HCl) at or near pH 7.0 for a time sufficient to extract the desired proteins. Preferably, the extraction is performed by stirring the demineralized bone powder with 4M GuHCl-0.01M Tris.HCl buffer (pH 7.0) in the presence of a proteolytic enzyme inhibitor such as phenylmethylsulfonylfluoride for 8 to 12 hours (hrs) between about 4° to 20° C. The proteins from demineralized bone powder can be extracted by contacting the demineralized bone powder with an appropriate GuHCl-Tris.HCl buffer for a time sufficient to obtain substantial quantities of the desired proteins. In a typical extraction of 100 grams of demineralized calf bone powder, approximately 1500 milligrams (mg) of total proteins are extracted in a three day extraction period with 4M GuHCl-0.01M Tris.HCl buffer (pH 7.0). In the process of the present invention, it has been found that more than 80 percent (%) of the total proteins obtained in a three day extraction can be extracted in the first 8 to 12 hrs with a 4M GuHCl-0.01M Tris.HCl buffer (pH 7.0). During the first 8 to 12 hrs of extraction typically more than 95% of the total low molecular weight protein population that can be obtained in a three day extraction is recovered. Most osteogenic activity is associated with these low molecular weight proteins. About 15 ml of the 4M GuHCl-0.01M Tris.HCl buffer (pH 7.0) solution is used per gram dry weight of demineralized bone powder. After the extraction period is complete, the extract is filtered, for example, over Whatman paper, and the filtrate concentrated by conventional procedures; in typical experiments, an Amicon ultrafiltration apparatus (Amicon Corporation, Lexington, Mass.) with a membrane filter with molecular cut-off size of approximately 5,000 daltons is used for the concentration step (that is, the membrane retains molecules having a molecular weight greater than approximately 5,000 daltons, for example, an appropriate Diaflo ® ultrafiltration membrane such as YM-5).

The various buffers, for example, the 4M GuHCl-0.01M Tris.HCl buffer, and solutions, for example, the 0.5N HCl solution, described herein are aqueous buffers or solutions in which the indicated materials are present in water at the indicated concentration. The protein components of the concentrated protein solution were fractionated using various conventional chromatographic techniques including high performance liquid chromatography (HPLC) as follows:

The initial protein fractionation was conveniently accomplished by chromatography on a Sepharose CL-6B (Pharmacia Chemicals, N.J.) column. In a typical experiment, the proteins extracted as described herein are concentrated by ultrafiltration to a concentration of about 25 to 40 mg/ml. The concentration of proteins in various extract preparations and column fractions were usually estimated by conventional means such as spectrophotometric measurement of the absorbance of the solutions at 280 nanometers (nm). An appropriate amount of the protein concentrate (an amount providing approximately 500 mg of protein) was applied to a 5 centimeter (cm)×90 cm Sepharose CL-6B column equilibrated with 4M GuHCl-0.01M Tris.HCl buffer (pH 7.0). The column is eluted with the 4M GuHCl-0.01M Tris.HCl buffer (pH 7.0) at a hydrostatic pressure head of between about 50 to 100 cm and individual fractions of 15 to 20 ml volume collected. A typical elution profile under the above conditions was obtained by measuring the absorbance of individual fractions at 280 nm and is shown in FIG. 1.

Figure 2:
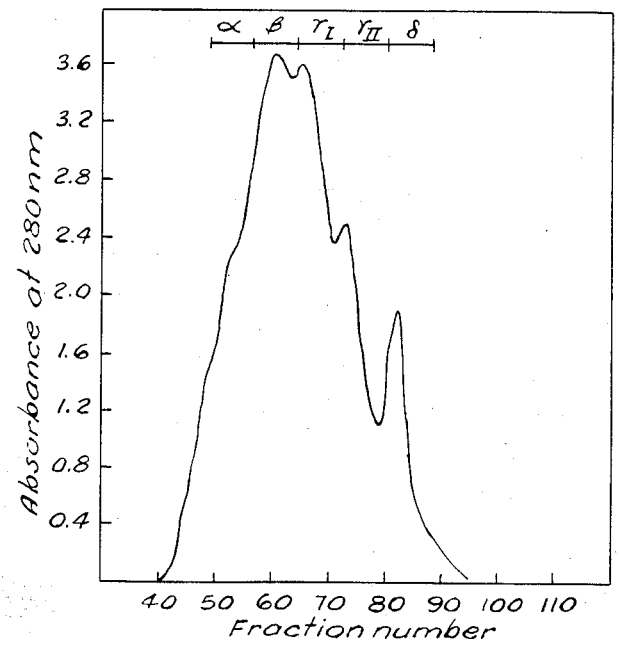
FIG. 2 represents the elution profile obtained by Sephacryl S-200 column Chromatography, in 4M GuHCl-0.01M Tris.HCl buffer (pH 7.0), of the proteins contained in the active fraction obtained from Sepharose CL-6B column chromatography.

The bone inducing activity of various fractions eluted from the Sepharose CL-6B column was measured, using the bone induction assay system described herein, and indicated that the pool of fractions identified as "C" in FIG. 1 contained the factors responsible for the osteogenic activity. Pool C, which consisted of pooled fractions V, VI and VII, was concentrated using conventional procedures. In a standard extraction, pool C obtained from the elution of the total proteins on the Sepharose CL-6B column represents about 40% of the total proteins obtained in an 8 to 12 hr extraction of demineralized calf bone powder with 4M GuHCl-0.01M Tris.HCl buffer (pH 7.0). Further fractionation was then achieved by chromatography on a Sephacryl S-200 (Pharmacia Chemicals, New Jersey) column. In a typical experiment, 75 to 100 mg of proteins from pool C are applied at a concentration of approximately 25 mg/ml to a 2.2 cm×115 cm Sephacryl S-200 column and the column eluted with 4M GuHCl-0.01M Tris.HCl buffer (pH 7.0) under a hydrostatic pressure head of between about 50 to 75 cm and individual fractions of approximately 4 ml in volume collected. A typical elution profile which was obtained under the above conditions is shown in FIG. 2.

Fractions from the Sephacryl S-200 column were pooled (see FIG. 2) and the resulting pooled materials arbitrarily identified as alpha ($\alpha$), beta ($\beta$), gamma I ($\gamma$I), gamma II ($\gamma$II) and delta ($\delta$).

Analysis of the proteins, using conventional discontinuous polyacrylamide gel electrophoresis in the presence of sodium dodecyl sulfate [Laemmli, U. K., Nature, Vol. 227, pp. 680–685 (1970)], contained in the respective alpha through delta pools allowed identification of several proteins. It was found that the alpha pool contained minor protein components of molecular weight higher than 50,000 daltons; the beta pool contained a major species at 38,000 to 40,000 daltons, some minor higher molecular weight contaminants, and small quantities of lower molecular weight protein species migrating between 14,000 and 30,000 daltons; the gamma I and gamma II pools contained four major size class species migrating at 31,000 to 35,000 daltons, at 22,000 to 25,000 daltons, at 16,000 to 18,000 daltons, and at 12,000 to 14,000 daltons; the delta pool contained mostly proteins in the 12,000 to 14,000 dalton range.

Measurement of activity in the bone induction assay essentially as described herein indicated that the gamma I and gamma II pools contained factors inducing bone formation.

To simplify the discussion concerning the final purification of the osteogenic factors a list of the protein species found in the beta, gamma and delta pools is presented in Table 1. As indicated previously, each of the respective major protein species was assigned an identifying code (P1, P2 and the like) as indicated in Table 1.

TABLE 1

| Major Species | | Minor Species | |
|---|---|---|---|
| Assigned Name | Estimated Molecular Weight $\times 10^{-3}$ | Assigned Name | Estimated Molecular Weight $\times 10^{-3}$ |
| P1 | 38–40 | | |
| P2 | 30–33 | | |
| | | PA | 28–30 |
| | | PB | 24 |
| P3 | 22–24 | | |
| | | PC | 19 |
| P4 | 16–18 | | |
| P5a | 13–14 | | |
| P5b | 14* | | |
| | | PD | 12 |

All primary molecular weight assignments of protein species are based on mobilities in discontinuous polyacrylamide gel electrophoresis with 13% acrylamide at pH 8.8 in the resolving gel in the presence of sodium dodecyl sulfate and a reducing agent. The minor protein species represented less than 10 to 15 percent of the total material in the respective samples analyzed on gels. *P5b migrates at about 10,000 daltons under nonreducing conditions which serves to distinguish P5a from P5b.

Final Purification of Bone Inducing Activity

The final purification was accomplished by reverse phase HPLC of the partially purified protein preparations, obtained from Sephacryl S-200 column chromatography, using a Beckman Altex HPLC controlled by a Model 421 microprocessor unit. Two approaches have been used.

A characteristic feature of some of the proteins, especially the P3 protein family described herein is the lack of solubility in the absence of a strong dissociating agent such as GuHCl. In addition, when multiple protein species were simultaneously present in a pool, the removal of GuHCl resulted in a coprecipitation of other proteins along with P3. A method was, therefore, developed where narrow pools consisting of only one or two major proteins were obtained from the Sephacryl S-200 column and used as the starting material for further purification by HPLC. In addition, in order to maximize the retention of proteins in solution, pools such as the ones described above were dialyzed directly against an aqueous solvent containing 0.1% trifluoroacetic acid (TFA) supplemented with acetonitrile (ACN) at concentrations of between 10% to 15% by volume. A conventional dialysis membrane tubing with molecular weight cut-off size of 3,500 daltons or lower is conveniently used in this procedure. Proteins soluble in the TFA:ACN solvent could then be conveniently obtained by removal of the insoluble material from each dialyzed pool by centrifugation. The soluble proteins at this point could be chromatographed on a reverse phase HPLC column such as the Protesil 300 octyl column described herein. In a typical experiment, the TFA:ACN soluble proteins obtained from the peak fractions in this manner were applied to a 0.46 cm × 25.0 cm Protesil 300 octyl column (Whatman) of 10 micron particle size equilibrated with 0.1% TFA:10% ACN. Proteins bound to the column under these conditions were eluted at a flow rate of 60 ml/hr using a linear 10% to 80% ACN gradient developed over 45 minutes. In a typical experiment, as indicated in FIG. 3A, P2 and P1 proteins were sequentially recovered with increasing ACN concentrations (depicted by the dashed line) from the gamma I peak. Similarly, P1 protein can be obtained from the beta peak while P5a and P5b are obtained from the delta peak. The P3 protein elutes between the gamma I and gamma II regions of the Sephacryl S-200 column. The P3 protein is found in both the soluble and the insoluble materials obtained by dialysis of appropriate fractions against TFA:ACN. The lack of solubility of the P3 protein thus yields essentially homogeneous P3 protein in the insoluble material. The P3 retained in solution in the TFA:ACN solvent can be further purified by reverse phase HPLC essentially as described above.

The second procedure to purify proteins to an essentially homogeneous state was designed to take advantage of the high degree of insolubility of certain proteins in the 35,000 to 14,000 dalton range, especially when they are present together at high concentrations (for example, approximately 10 mg/ml). In this procedure proteins eluting in the gamma I and gamma II pools from the Sephacryl S-200 column chromatography (that is, the pools where the bone inducing activity is found) were concentrated to approximately 10 mg/ml. The material was rapidly dialyzed [for example, six changes each of 4 liters every 2 to 3 hrs, (using dialysis tubing with a molecular cut-off size of 2,000 daltons)] against deionized distilled water at 15° to 23° C. Precipitated proteins were collected by centrifugation and washed several times with deionized distilled water keeping the concentration of protein at higher than 10 mg/ml of washing water. The principal constituents of this precipitated material were found to be P2, P3, P4 and P5a; small amounts of P1 protein was found in variable quantities in some cases. The final pellet was dissolved in 0.1% TFA with 15% ACN and the solubilized material was applied to a Protesil 300 octyl column. Increasing ACN concentration eluted the P2, P3, P4 and P5a proteins as shown in FIG. 3B, a typical elution profile.

Figure 3:
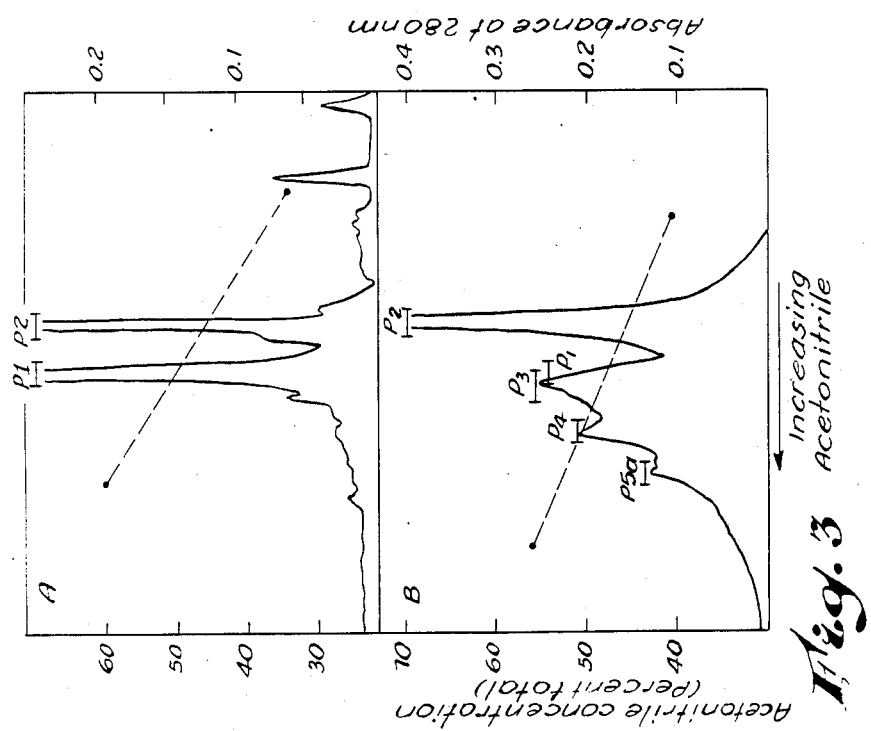
FIG. 3 represents the elution profile of proteins present in the active pool from Sephacryl S-200 column chromatography on a reverse phase Protesil 300 octyl column using an acetonitrile gradient for the elution of proteins.

Each of the major protein species described in Table 1 was further purified by rechromatographing on the Protesil 300 octyl column. Pools of fractions obtained as indicated in FIG. 3 were concentrated by lyophilization and redissolved in 0.1% TFA and about 10 to 20% ACN depending upon the particular lyophilized material and reapplied to the Protesil 300 octyl column. The proteins were eluted from the column using a linear 10% to 80% ACN gradient at a flow rate of 60 ml/hr under conditions as previously described herein except that the proteins were eluted over a longer period thus resulting in numerous individual fractions. The purity of each of the protein fractions was determined using conventional discontinuous PAGE. Those fractions which showed only one major species were used for further chemical and biological characterizations. Typically these fractions were lyophilized and stored as lyophilized powders.

Figure 4:
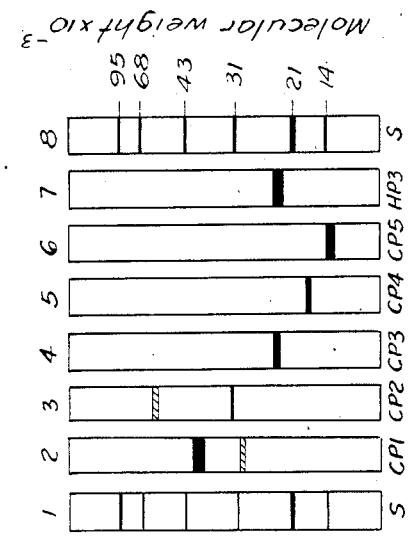
FIG. 4 represents the results of electrophoretic analysis of purified bone matrix proteins on discontinuous sodium dodecyl sulfate-polyacrylamide gels in the presence of a reducing agent.

FIG. 4 depicts the results of a typical discontinuous gel electrophoretic analysis on sodium dodecyl sulfate-polyacrylamide gels. The analysis was performed on a discontinuous polyacrylamide gel system in the presence of sodium dodecyl sulfate and a reducing agent where the resolving gel was 13% in acylamide and 0.35% in bis-acrylamide crosslinker at a pH of 8.8. The gel was run at 50 volts for 30 minutes followed by 7 hrs at 100 volts. Protein bands were visualized by staining with coomassie brilliant blue R. Columns 1 and 8 depict gels with the following standard molecular weight markers: 95,000 (phosphorylase A), 68,000 (bovine serum albumin), 43,000 (ovalbumin), 31,000 (carbonic anhydrase), 21,000 (soybean trypsin inhibitor), and 14,000 (ribonuclease); Columns 2, 3, 4, 5 and 6 show, respectively, the P1, P2, P3, P4 and P5 proteins (CP1 thus CP5) from demineralized calf bone powder; and Column 7 and P3 protein (HP3) from demineralized human bone powder. Portions shaded with oblique lies are bands of low concentration.

The amino terminus sequences of the P2, P3 and P4 proteins obtained from calf bone were investigated using the following procedure:

Amino terminal sequences were determined on an Applied Biosystems Model 470A Gas Phase Protein Sequencer. Reconstituted samples were applied to the loading disc in a volume of 30 microliters ($\mu$l) in a solvent appropriate to dissolve the protein (typically trifluoroacetic acid). Polybrene was added to the disc prior to the addition of the sample and the reaction vessel precycled for 12 cycles to condition the Polybrene/disc carriers. The Edman degradation and resultant conversions were performed automatically by the instrument. The amino acid derivatives were identified on a Hewlett-Packard High Performance Liquid Chromatograph Model 1084B using an acetate/acetonitrile:methanol gradient as described previously, see Thomas, K. A., et al., J. Biol. Chem., Vol. 256, pp. 1947–1955 (1981). A Beckman C18 microsphere reverse phase column was employed for the identification. The gas sequencer and HPLC program employed allowed identification of all 20 amino acid derivatives in each sample.

The partial amino terminus sequence of the P3 protein was determined to be $H_2N$-Phe-Pro-Val-Tyr-Asp-Tyr-Ser-Pro-Ala-Arg-Leu-Lys-Glu-Ala.

The partial amino terminus sequence of the P2 protein was determined to be $H_2N$-TrP-?-Pro-Tyr-?-Trp.

The partial amino terminus sequence of the P4 protein complex indicated that two major components were present with the following sequences:

H₂N-Ala-Glu-Pro-?-?-Tyr;

H₂N-Pro-Glu-Pro-?-?-Tyr.

The identity of the respective amino acid residues in the partial amino terminus sequences is represented using conventionally accepted abbreviations and the "?" indicates an amino acid residue which remains unidentified.

Following the extraction and purification procedure essentially as described herein, a protein was obtained from demineralized human bone powder also having a molecular weight of approximately 23,000 daltons and designated as human P3 protein. This protein purified to an essentially homogeneous state also induced the formation of bone when implanted. The human P3 protein obtained from human bone appears to be closely related to the calf P3 protein. The respective calf and human P3 proteins show the following similarities:

(1) both are extracted and purified following similar procedures, both are only sparingly soluble in water in the absence of a strong dissociating agent;

(2) each has the demonstrated ability to induce bone formation in the bone induction assay system;

(3) each has the same apparent molecular weight in the discontinuous sodium dodecyl sulfate-polyacrylamide gel electrophoresis system;

(4) the proteins are immunologically related since antibodies prepared against the calf bone-derived P3 protein form immunecomplexes with the human bone-derived P3 protein; and (5) amino acid analyses show significant similarities as described in Table 2.

Amino acid compositions for the calf P3 and human P3 proteins were determined from acid hydrolysates prepared with redistilled 6N hydrochloric acid (110° C., 24 hrs). The tubes were evacuated prior to sealing to eliminate oxygen. Following removal of the 6N hydrochloric acid by evaporation and reconstitution in citrate buffer, the hydrolysates were analyzed, on a Durrum D500 (Dionex) automatic amino acid analyzer. Standard operating procedures were used as described by Benson, J. R., et al., "Amino Acid Analysis of Peptides" in *Peptides: Analysis, Synthesis, Biology* (E. Gross and J. Meienhofer, eds.) Academic Press, New York, Vol. 4, pp. 217-260 (1981). The quantitative data produced was converted to residues/mole of protein based upon the molecular weights estimated by conventional PAGE.

The amino acid composition data in Table 2 concerning the human P3 and the calf P3 proteins is based on two runs per protein (duplicate analyses on a single preparation of each protein) on a Durrum D500 amino acid analyzer.

Table 2 also contains the amino acid compositions of several proteins previously described in the art, namely, a 17,000 to 18,000 dalton bone morphogenetic protein from calf bone described by Urist, M. R. et al., Science, Vol. 220, pp. 680-686 (1983); a 17,000 to 18,000 dalton bone morphogenetic protein from human bone, Urist, M. R., et al., Proceedings of the Society of Experimental Biology and Medicine, Vol. 173, pp. 194-199 (1983); a 23,000 dalton bone morphogenetic protein from rabbit dentin, Conover, M. A., and Urist, M. R., The Chemistry and Biology of Mineralized Connective Tissues, Elsevier North Holland, Inc., pp. 597-606 (1981); and a calf bone-derived protein which does not induce osteogenesis and has a molecular weight of 24,000 daltons (calf bone 24K protein), Urist, M. R., et al., Science, Vol. 220, pp. 680-686 (1983).

TABLE 2

A Comparison of the Amino Acid Compositions of Several Bone Derived Proteins

| Amino Acid | Osteogenic Proteins of the Invention | | Previously Reported Proteins | | | |
|---|---|---|---|---|---|---|
| | P3 Human | P3 Calf | Bone Morphogenetic Proteins | | | Calf Bone 24K Protein |
| | | | Calf | Human | Rabbit | |
| Asp (+Asn) | 16 | 22 | 17 | 14 | 34 | 30 |
| Thr | 11 | 10 | 7 | 5 | 8 | 13 |
| Ser | 13 | 14 | 19 | 14 | 25 | 20 |
| Glu (+Gln) | 27 | 25 | 18 | 18 | 28 | 18 |
| Pro | 16 | 13 | 12 | 7 | 9 | 13 |
| Gly | 19.5 | 17 | 15 | 43 | 17 | 20 |
| Ala | 14 | 12 | 11 | 12 | 9 | 16 |
| Val | 14 | 14 | 9 | 8 | 4 | 10 |
| Met | 3 | 5 | 2.5 | 2 | 1 | 4 |
| Ile | 8 | 6 | 8 | 6 | 4 | 8 |
| Leu | 17 | 12 | 12.5 | 12 | 7 | 14.5 |
| Tyr | 16 | 19 | 7 | 5 | 5 | 12 |
| Phe | 10 | 8 | 8 | 5 | 5 | 11 |
| His | 5 | 6 | 3 | 3 | 3 | 8 |
| Lys | 7 | 7 | 7 | 7 | 10 | 6 |
| Arg | 13 | 15 | 8 | 12 | 8 | 6 |
| Cys(½) | N.D. | N.D. | 3 | 3.5 | 1 | 0 |
| Trp | N.D. | N.D. | N.D. | N.D. | N.D. | N.D. |

The numbers represent approximate number of residues (to the nearest whole number) of the indicated amino acids per mole of the respective proteins whose molecular weights were estimated by independent methods conventionally used, such as polyacrylamide gel electrophoresis. The numbers for the P3 proteins of this invention are within experimental errors in the art of amino acid composition analysis. N.D. means no determination was made of the indicated amino acid.

The calf and the human P3 proteins in an essentially homogeneous state, each, when implanted in rats following the bioassay system described herein, induces the formation of bone at the implant site in approximately 3 weeks. It appears that the members of the P3 protein family purified from different mammals will show osteogenic activity in mammals in general. Thus the P3 proteins represent a family of immunologically related proteins considered to be the primary osteogenic factors.

Bone Induction Assay System

To determine the osteogenic activity of test protein fractions or proteins a procedure such as the following can be used. Bone matrix powder (75 to 500μ size) is demineralized as described herein and then extracted sequentially three times, each with 15 to 20 ml of 4M GuHCl per gram of demineralized bone powder. The extracted matrix is extensively washed with water, followed by ethanol and ether and then the powder is dried. This powder, when implanted in a test animal, such as a rat, does not induce osteogenesis and is called inactive bone matrix (IBM). In order to measure the activity of a protein preparation, the IBM powder is mixed with an aqueous solution or suspension of the protein and the water removed by lyophilization. The reconstituted matrix is then packed in gelatin capsules an implanted subcutaneously near the thigh muscles of young (one to two months old) rats. Varying amounts of protein preparations are used together with a constant amount of IBM in each capsule to determine the efficacy of the different protein preparations. Osteogenic activity in each implant is estimated by two approaches, (a) measuring the level of the enzyme alkaline phosphatase in the implant tissues at 17 to 20 days following implantation and (b) performing a histologic examination of a 5 to 7 micron thick section of the tissue developed at the implant site following staining of paraffin-fixed sections of this tissue with toluidine blue (stains cartilage matrix), hematoxylin-eosin (resolves fibrous, cartilaginous and bone tissues) and von Kossa silver stain (for calcified matrix of bone tissue).

The level of alkaline phosphatase is measured since active bone formation is characteristically preceded by a significant surge of this enzyme and continued formation of bone is accomplished by a stable elevated level of alkaline phosphatase activity compared to that found in non-bone fibrous tissue surrounding the implants. An approximate quantitation of the levels of bone inducing activity in a protein preparation has been obtained by quantitating the level of alkaline phosphatase per unit weight of implant tissue. In practice, the implant tissue is homogenized in an appropriate buffer such as Tris-saline, dissociated with a nonionic detergent and the solubilized enzymes that are released from the tissue are obtained by removing the debris using centrifugation. The levels of alkaline phosphatase are quantitated by measuring the conversion of paranitrophenylphosphate to paranitrophenol catalyzed by dilutions of the test extract and calculating from a standard curve of known enzyme activity.

In bioassay studies, protein pools from the Sephacryl S-200 column were reconstituted with IBM and implanted subcutaneously in rat thighs. Measurement of alkaline phosphatase activity and histological evaluation of sections of explants removed 17 to 20 days after implantation, showed that the P1 and the P5a-P5b proteins do not have bone inducing activity. The bioassay studies indicated the presence of maximum osteogenic activity in proteins in pools gamma I and gamma II. The three major components of the gamma fractions, that is, the P2, the P3 and the P4 proteins were purified to an essentially homogeneous state using reverse phase HPLC as described above. The purified proteins, either singly or in a complete mixture, were reconstituted with inactive bone matrix and a bone induction assay performed. The results are shown in Table 3.

TABLE 3

|  | Alkaline Phosphatase (units/g) | Histology |
|---|---|---|
| IBM* Alone | <5 | Fibrous Tissue |
| IBM + 750 μg P2 protein | <5 | Fibrous Tissue |
| IBM + 750 μg P3 protein | 78 | New Bone |
| IBM + 1000 μg P4 protein | <5 | Fibrous Tissue (a small trace of cartilage) |
| IBM + 250 μg each of P2, P3 and P4 proteins | 63 | New Bone |

*"IBM" means Inactive Bone Matrix.
"<" means less than.

The data in Table 3 indicates that the P3 protein alone induced the formation of bone. Implants containing the P3 preparation developed into tissues that contained high levels of alkaline phosphatase enzyme activity. In contrast, implants prepared by reconstituting with either the P2 or the P4 preparation failed to produce detectable bone. When all three proteins were used in combination, significant bone formation was observed and high levels of alkaline phosphatase enzyme were obtained with one-third the amount of P3 protein (as compared to the P3 protein implant alone). It thus appears that at low concentrations of P3 protein, the presence of the P2 and/or the P4 protein provides enhancement of osteogenesis induced by the P3 protein.

In using the active preparations described herein an osteogenic amount of the protein and/or active polypeptide and/or immunologically related entity, with or without a pharmaceutically acceptable carrier, is administered at or in the proximity of the site in the mammal at which bone induction is desired. Administration will depend on the age, condition, sex and other characteristics of the subject to be treated. Preferred administration is by implantation, local injection or time controlled delivery using microcapsules, or other devices. Dosages will depend on the site and configuration of the area to be healed, such as, for example, a fracture zone. For example, a 5 cubic millimeter bone chip can be obtained with about 100 to 200 micrograms (μg) of P3 administered or implanted locally in the form of an implant in about 100 mg of IBM.

Active preparations can include other suitable bioactive materials such as growth factors, chemotactic agents, steroids, antibiotics, anti-inflammatory agents and the like.

What is claimed is:

1. A method for isolating a preparation of an osteogenic protein which is a member of the P3 family of immunologically related proteins, said preparation characterized by being essentially homogeneous with respect to a molecular weight of from about 22,000 daltons to about 24,000 daltons from demineralized bone tissue comprising:
   (a) treating said demineralized bone tissue under aqueous conditions with a solubilizing agent for said osteogenic protein and thereby extracting the osteogenic factor into solution with said solubilizing agent;
   (b) subjecting said solution to size fractionation to recover a concentrated pool of proteins of molecular weight between about 12,000 daltons and 40,000 daltons;
   (c) subjecting said concentrated pool to a dialysis step comprising either (i) dialysis of said concentrated pool against an aqueous solvent containing trifluoroacetic acid and acetonitrile and removal of the insoluble material to obtain a soluble fraction or (ii) dialysis against deionized water to form an insoluble pellet and solubilization of said pellet with an aqueous solvent comprising trifluoroacetic acid and acetonitrile to obtain a soluble fraction;
   (d) subjecting the soluble fraction of step (c) to reverse phase high performance liquid chromatography; and
   (e) recovering a preparation of an osteogenic protein.

2. The method of claim 1 wherein said solubilizing agent is guanidinium-hydrochloride.

3. The method of claim 1 wherein the solution isolated in step (a) is subjected to size fractionation to recover a concentrated pool of proteins of molcular weight between about 16,000 daltons and about 25,000 daltons.

4. The method of claim 1 wherein the size fractionation of step (b) is conducted by gel filtration.

5. A preparation of an osteogenic protein which is a member of the P3 family of immunologically related proteins, said preparation characterized by being essentially homogeneous with respect to a molecular weight of from about 22,000 daltons to about 24,000 daltons and by the capacity, in such essentially homogeneous state, of promoting osteogenesis in a manual prepared according to the process of claim 1.

6. The preparation of claim 5 which is isolated from bovine bone.

7. The preparation of claim 5 which is isolated from human bone.

8. The preparation of claim 5 which is isolated from porcine bone.

* * * * *

UNITED STATES PATENT AND TRADEMARK OFFICE
CERTIFICATE OF CORRECTION

PATENT NO. : 4,804,744
DATED : February 14, 1989
INVENTOR(S) : Arup Sen

It is certified that error appears in the above-identified patent and that said Letters Patent is hereby corrected as shown below:

Col. 1, line 13, change "noncollageous" to --noncollagenous--;

col. 1, line 55, change "matris-associated" to --matrix-associated--;

col. 2, line 13, change "procedure" to --procedures--;

col. 4, line 2, change "Chromatography" to --chromatography--;

col. 5, line 18, delete the comma after "Thus";

col. 5, line 33, after "one" add --or--;

col. 6, line 37, delete "of" (first occurrence);

col. 10, line 38, change "and" to --the--;

col. 10, line 39, change "lies" to --lines--;

col. 10, lines 48-49, change "tri-flueroacetic" to --tri-fluoroacetic--;

col. 13, line 13, change "accomplished" to --accompanied--;

col. 15, line 2, change "manual" to --mammal--.

Signed and Sealed this

Sixteenth Day of June, 1992

Attest:

DOUGLAS B. COMER

*Attesting Officer*　　*Acting Commissioner of Patents and Trademarks*